(12) United States Patent
Nouadje et al.

(10) Patent No.: US 7,297,244 B2
(45) Date of Patent: Nov. 20, 2007

(54) CAPILLARY ELECTROPHORESIS SYSTEMS AND ADDITIVES

(75) Inventors: Georges Nouadje, Evry (FR); Frédéric Robert, Mennecy (FR)

(73) Assignee: Sebia (FR)

( * ) Notice: Subject to any disclaimer, the term of this patent is extended or adjusted under 35 U.S.C. 154(b) by 162 days.

(21) Appl. No.: 10/052,931

(22) Filed: Jan. 18, 2002

(65) Prior Publication Data
US 2002/0162744 A1 Nov. 7, 2002

(30) Foreign Application Priority Data
Jan. 19, 2001 (FR) .................................. 01 00762

(51) Int. Cl.
*G01N 27/447* (2006.01)
(52) U.S. Cl. ...................... 204/451; 204/468
(58) Field of Classification Search ................ 204/451, 204/468, 601; 435/7.1; 436/517; 252/62.2
See application file for complete search history.

(56) References Cited

U.S. PATENT DOCUMENTS

| | | | |
|---|---|---|---|
| 4,714,677 A * | 12/1987 | Keyes ........................ 435/183 |
| 4,769,408 A * | 9/1988 | Ogawa et al. ............... 204/469 |
| 4,778,909 A * | 10/1988 | Karger et al. ................ 556/450 |
| 4,872,865 A * | 10/1989 | Bloebaum et al. ............. 604/28 |
| 4,965,188 A * | 10/1990 | Mullis et al. .................... 435/6 |
| 5,599,433 A * | 2/1997 | Keo et al. .................... 204/451 |
| 5,753,094 A * | 5/1998 | Alter et al. .................. 204/451 |
| RE36,011 E | 12/1998 | Grushka et al. |
| 5,928,484 A * | 7/1999 | Bellon et al. ................ 204/469 |
| 5,938,930 A * | 8/1999 | Hjerten et al. ............... 210/656 |
| 2002/0195341 A1* | 12/2002 | Robert ........................ 204/451 |

FOREIGN PATENT DOCUMENTS

| | | |
|---|---|---|
| EP | 0 518 475 A | 12/1992 |
| EP | A 0 518 475 | 4/1997 |
| JP | 2-12059 A * | 1/1990 |
| WO | WO 00 70334 A | 11/2000 |

OTHER PUBLICATIONS

Lauer et al, "Capillary Zone Electrophoresis of Proteins in Untreated Fused Silica Tubing," Anal. Chem., vol. 58, pp. 166-170, (1986).*

* cited by examiner

*Primary Examiner*—Alex Noguerola
(74) *Attorney, Agent, or Firm*—Lerner, David, Littenberg, Krumholz & Mentlik, LLP

(57) ABSTRACT

Capillary electrophoresis systems, reagents, and processes for analyzing a sample which includes at least one protein constituent are disclosed. The processes involve introducing the sample into a capillary tube containing a buffer system, wherein said buffer system includes at least one additive having a hydrophobic interaction with said at least one protein constituent and providing said at least one protein constituent with at least one negative charge thereby modifying the electrophoretic mobility.

24 Claims, 3 Drawing Sheets

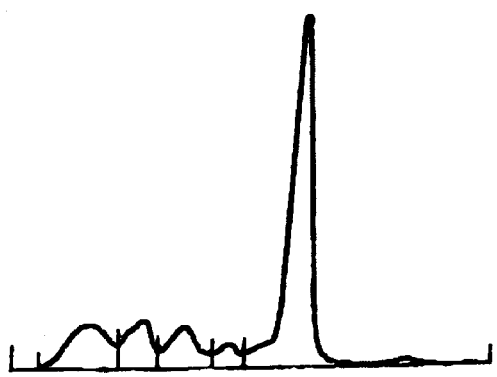
FIG_1
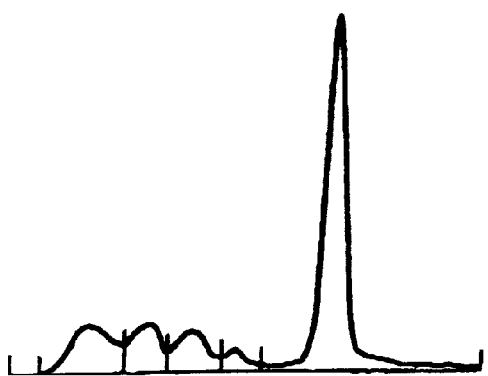
FIG_2
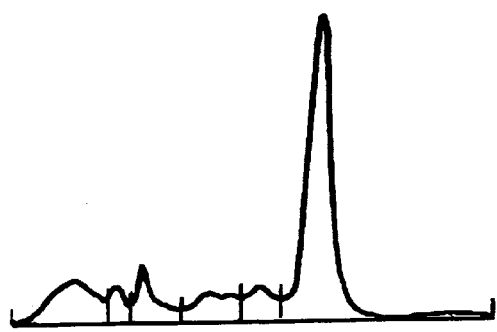
FIG_3
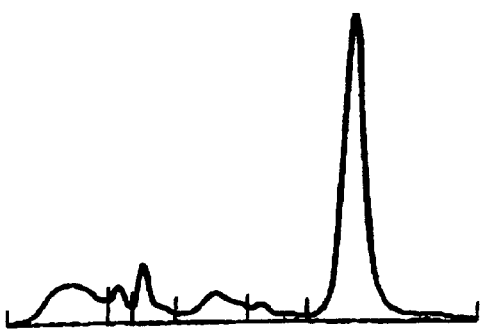
FIG_4
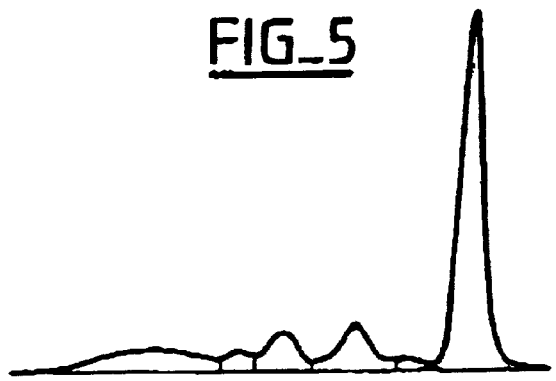
FIG_5

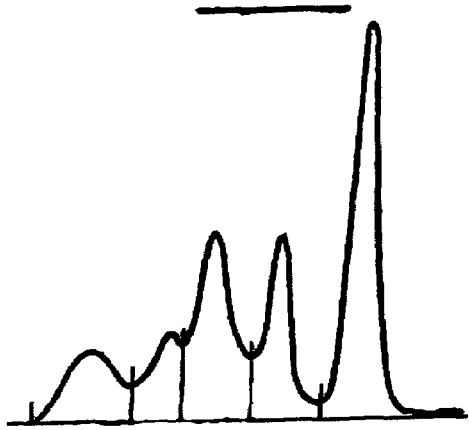
FIG_6
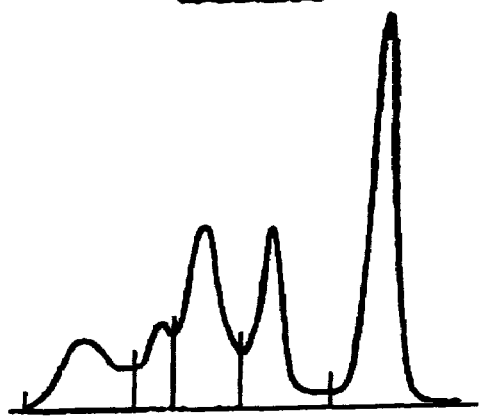
FIG_7
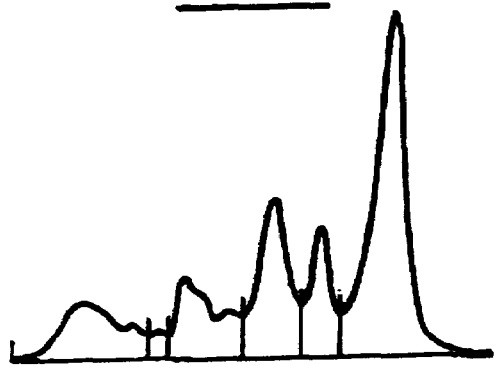
FIG_8
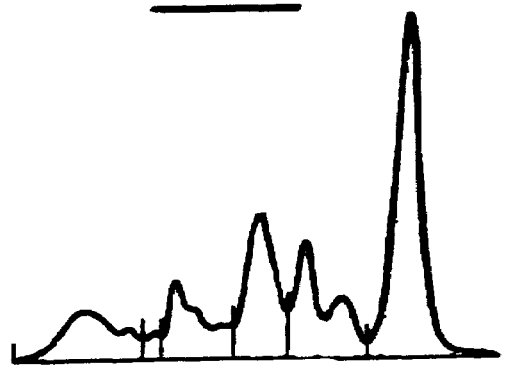
FIG_9
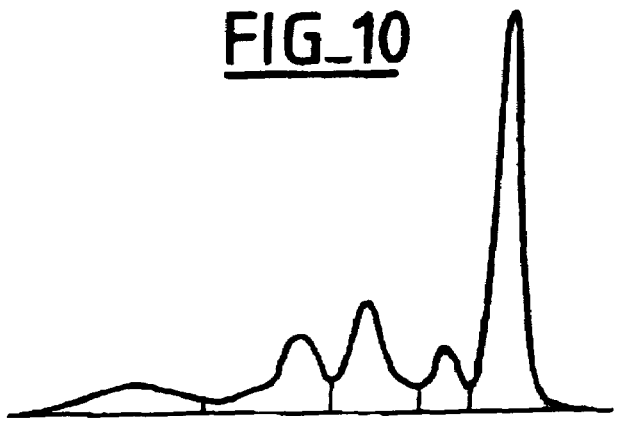
FIG_10

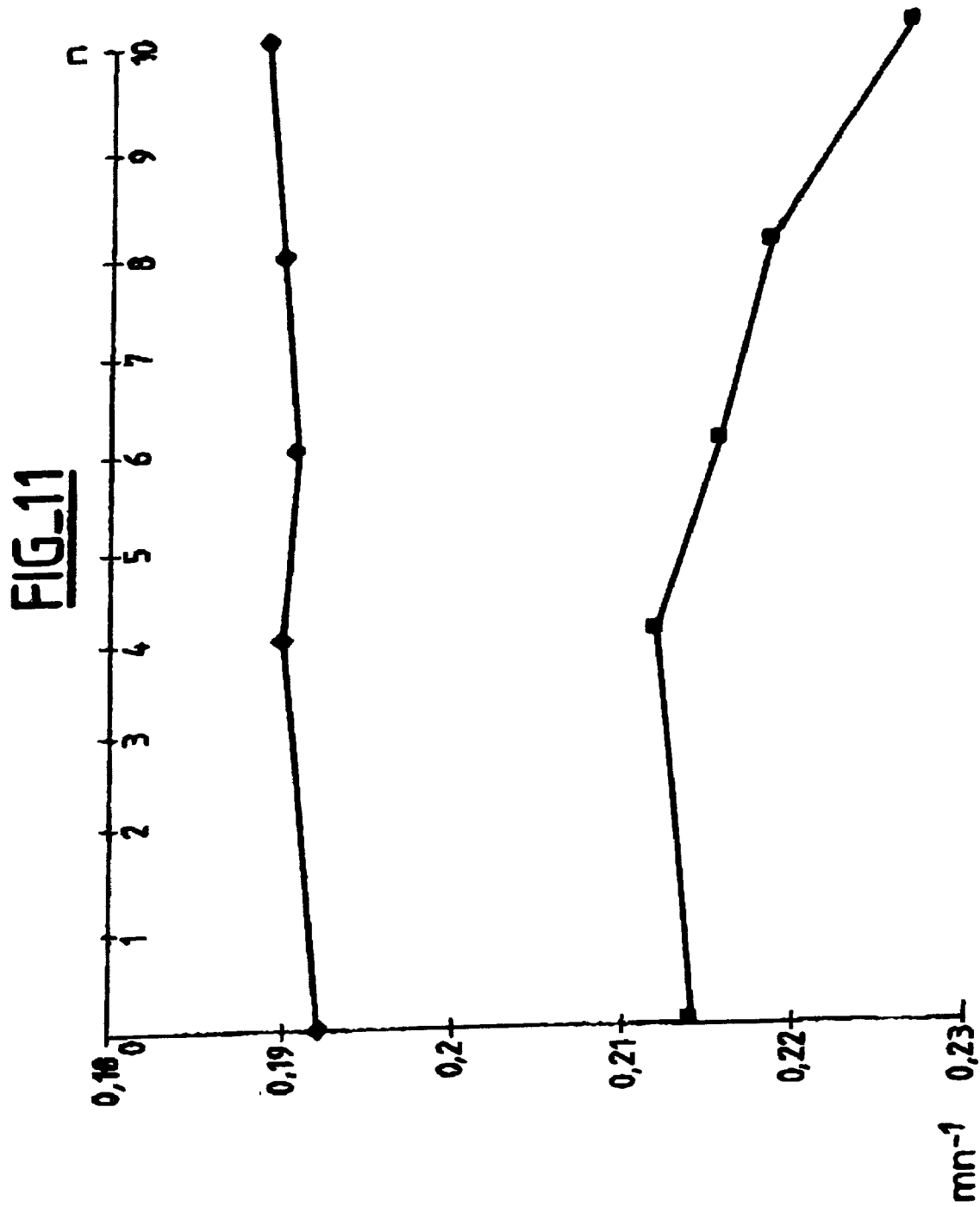
FIG_11

CAPILLARY ELECTROPHORESIS SYSTEMS AND ADDITIVES

CROSS REFERENCE TO RELATED APPLICATIONS

The present application claims priority from French Application No. 01/00762, filed Jan. 19, 2001, all of which is incorporated herein by reference.

The present invention relates to a process for separating proteins and peptides by capillary electrophoresis and to buffer compositions comprising an additive for use in such separation.

The proteins in biological fluids such as serum are analysed for analytical for diagnostic purposes and in particular, usually by separating the proteins by electrophoresis, either gel electrophoresis or capillary electrophoresis. One advantage of capillary electrophoresis lies in the fact that only tiny quantities of biological fluids are required for analysis. Further, separation using that technique can be very rapid, because high voltages can used without the sample heating up too much during separation.

To separate blood proteins, capillary electrophoresis is conventionally carried out with alkaline buffers. Usually, the protein profiles obtained comprise five or six fractions, namely the albumin fraction, the $\alpha_1$ and $\alpha_2$ globulin factions, the $\beta$ globulin fraction or the $\beta_1$ and $\beta_2$ globulin fractions, and the $\gamma$ globulin fraction.

Such separation can be carried out using capillary electrophoresis with the aid of buffer systems and techniques such as those described in United States Reissued patent U.S. Re. Pat. No. 36 011 or European patent EP-A-0 518 475.

Until now, however, separating albumin and $\alpha_1$ globulin by capillary electrophoresis has been unsatisfactory.

The Applicant has now demonstrated that improved separation, in particular albumin/$\alpha_1$ globulin separation, can be achieved by employing an additive for the buffer system, which additive comprises an anionic pole with a pH of more than 9 and a hydrophobic portion. Such additives are capable of hydrophobic interactions with one or more protein constituents and are also capable of providing the protein constituent or constituents with one or more negative charges and of modifying the electrophoretic mobility.

Thus, the invention concerns an alkaline pH, free solution capillary electrophoresis method for analysing samples comprising protein constituents, in which the sample is introduced into a capillary tube containing a buffer system, said buffer system further comprising at least one additive that is capable of hydrophobic interaction with one or more protein constituents and capable of providing said protein constituent or constituents with one or more negative charges and of modifying the electrophoretic mobility. This step is generally followed by separating the protein constituents by migration and detecting the constituents.

The invention also concerns a method for separating protein constituents in samples comprising albumin and the following Fractions: $\alpha_1$; $\alpha_2$; $\beta$ (or $\beta_1$ and $\beta_2$); and $\gamma$ globulin, by electrophoresis in a buffer system, in which the buffer system comprises a further additive that is at least capable of a hydrophobic interaction with he albumin.

The present invention also concerns a method for electrophoretic separation, by alkaline pH, free solution capillary electrophoresis, of protein constituents in a liquid sample, in which method the sample comprising said constituents is passed into a capillary containing a buffer system further comprising at least one additive, the additive being a compound comprising an anionic pole with a pH of more than 9 and a hydrophobic portion The compounds that can be used as an additive to the capillary electrophoresis buffer system of the invention are capable of a hydrophobic interaction with albumin; these compounds can, for example, be anionic surfactants such as those used in MECC (micellar electrokinetic capillary chromatography), but at a concentration that is below their critical micellar concentration. In the present invention, we use these compounds in free solution CE: the compound provides the albumin with a negative charge by hydrophobic interaction between the hydrophobic residues of the albumin and the hydrophobic portion of these compounds, thus reducing the mobility of the albumin compared with that of the other proteins. One consequence is improved separation of albumin from the $\alpha_1$ fraction.

Finally, the invention concerns electrolyte compositions for capillary electrophoresis comprising at least one buffer and an additive that is capable of hydrophobic interaction with albumin, in a suitable support.

As will become clear from the examples, the use of the additives of the invention allows improved separation of the albumin and $\alpha_1$ globulin fractions. It also improves the base line return between these two fractions compared with the normal buffers.

Other characteristics and advantages of the invention will become clear from the following detailed description made with reference to the accompanying drawings and examples.

FIG. 1 shows an electropherogram of normal human serum analysed by capillary electrophoresis using a glycine buffer.

FIG. 2 shows an electropherogram of normal human serum analysed by capillary electrophoresis using the same glycine buffer with an additive of the invention.

FIG. 3 shows an electropherogram of normal human serum analysed by capillary electrophoresis using a borate buffer.

FIG. 4 shows an electropherogram of normal human serum analysed by capillary electrophoresis using the same borate buffer with an additive of the invention.

FIG. 5 shows an electropherogram of normal human serum obtained by agarose gel electrophoresis.

FIG. 6 shows an electropherogram of serum from a patient presenting with an acute inflammatory syndrome, obtained by capillary electrophoresis using a glycine buffer.

FIG. 7 shows an electropherogram of serum from a patient presenting with an acute inflammatory syndrome, obtained by capillary electrophoresis using the same glycine buffer with an additive of the invention.

FIG. 8 shows an electropherogram of serum from a patient presenting with an acute inflammatory syndrome, obtained by capillary electrophoresis using a borate buffer.

FIG. 9 shows an electropherogram of serum from a patient presenting with an acute inflammatory syndrome, obtained by capillary electrophoresis using the same borate buffer with an additive of the invention.

FIG. 10 shows an electropherogram of serum from a patient presenting with an acute inflammatory syndrome, obtained by agarose gel electrophoresis.

FIG. 11 shows the mobility of the $\alpha_1$ globulin fraction and that of the albumin fraction for various lengths of the carbon chain of an allylsulphonate added to a borate buffer.

Additives for the buffer in accordance with the invention that are capable of interacting with the hydrophobic portion of albumin that can be cited are compounds comprising an anionic pole with a pH of more than 9 and a hydrophobic portion. The hydrophobic portion can be composed of at least one alkyl chain, which may or may not be branched, containing 4 to 22 carbon atoms, namely 4 to 20 carbon atoms, and/or at least a combination of 1 to 10 cyclic groups, which groups may be aromatic or non aromatic. Preferably, combinations of 1 to 4 cyclic groups are used. As will be readily understood by the skilled person, this hydrophobic portion can comprise residues or functions that do not essentially modify its hydrophobic nature, such as one or more hydroxyl or amine functions, for example.

The anionic pole can be constituted by one or more of the chemical groups or functions from the following list: sulphonates, carboxylates, sulphates, phosphates, carbonates.

The following can in particular be cited: cholates, $C_6$ to $C_{22}$ alkyl-mono-, di- or tri- sulphonates, tetradecenesulphonate, naphthalenesulphonates, $C_6$ to $C_{22}$ alkylmono-, di- or trioxylates, $C_6$ to $C_{22}$ alciboxysulphonates, naphthalenecarboxylates, $C_4$ to $C_{14}$ alkylsulphates, $C_4$ to $C_{14}$ alkylcarbonates, benzenesulphonates and benzenecarboxylates. The above di- and tri-carboxylates, di- and tri-sulphonates and carboxysulphonates are thus combinations of one or more carboxylate or sulphonate functions on $C_6$ to $C_{22}$ alkyl chains. Non limitative examples thereof are the 1,2,3-nonadecanetricarboxylic acid (three carboxylate functions and a $C_{19}$ alkyl chain), the 2-methyl-2-sulfooctadecanoic acid (one carboxylate function and one sulfonate function and a $C_{18}$ alkyl chain) and the 1,12-dodecanedicarboxylic acid (two carboxylate functions and a $C_{12}$ alkyl chain).

$C_4$ to $C_{10}$ alkylsulphonates are more specifically cited amongst the $C_6$ to $C_{22}$ alkyl-mono-, di- or tri- sulphonates and the $C_4$ to $C_{10}$ alkylcarboxylates amongst the $C_6$ to $C_{22}$ alkyl-mono-, di- or tri- carboxylates, Within the above denominations, the alkyl radicals are preferably linear.

Biological buffers can be used as additives according to the invention. Particularly zwitterionic buffer of the Good type can be cited, as CAPS (3-cyclohexylamino-1-propanesulphonic acid) and CHES (2-(N-cyclohexylamino)ethanesulphonic acid).

Other zwitterionic biological buffer can be used within the context of the invention. The amino acid buffers are however not intended as a buffer or additive according to the present invention.

Preferred additives from those cited above are $C_6$ to $C_{10}$ alkylsulphonates, and of the $C_6$ to $C_{10}$ alkylsulphonates, octanesulphonate is preferred.

These compounds are known per se and are commercially available. They can be in the acid or salt form.

The term "sample in accordance with the invention" means the biological sample to be analysed, diluted with a suitable diluting solution or buffer system, for example, or pure.

The sample for analysis can be any biological liquid from healthy humans or human patients. The human biological liquids can be normal or abnormal serum, and also haemolysed serum, plasma, urine, or cerebro-spinal fluid. In addition to human biological samples, it is possible to analyse samples of animal origin. The samples can also be synthetic proteins, and the method of the invention is then intended for production control, for example.

The additives of the invention are of particular application for analysing serum, and for separating seric proteins in samples from humans.

In serum samples, the seric proteins to be separated are primarily albumin and the $\alpha_1$; $\alpha_2$; $\beta$ (or $\beta_1$ and $\beta_2$); and $\gamma$ globulin fractions.

The buffer system can be any known buffer system adapted to the desired separation, for use in electrophoresis in general and capillary electrophoresis in particular. Examples that can be cited are borate, phosphate and carbonate buffers, buffers based on amino acids and buffers known as biological buffers.

Examples of biological buffers that can be cited are those known as bis-TRIS (2-bis[2-hydroxyethyl]amino-2-hydroxymethyl-1,3-propanediol), ADA (N-[2-acetamido]-2-iminodiacetic acid), ACES (2-[2-acetamino[-2-aminoethanesulphonic acid), PIPES (1,4-piperazinediethanesulphonic acid), MOPSO (3-[N-morpholino]-2-hydroxypropanesulphonic acid), bis-TRIS PROPANE (1,3-bis[tris(hydroxymethyl)methylaminopropane]), BES (N,N-bis[2-hydroxyethyl]-2-aminoethanesulphonic acid), MOPS (3-[N-motpholino]propancsulphonic acid), TES (2-[2-hydroxy-1,1-bis(hydroxymethyl)ethylamino]ethanesulphonic acid), HEPES (N-[2-hydroxyethyl]piperazine-N'-(2-ethanesulphonic)acid), DIPSO (3-N,N-bis[2-hydroxyethyl]amino-2-hydroxypropanesulphonic acid), MOBS (4-N-morpholinobutanesulphouic acid), TAPSO (3[N-tris-hydroxymethyl-methylamino]-2-hydroxypropanesulphonic acid), TRIS (2-amino-2-[hydroxymethyl]-1,3-propanediol), HEPPSO (N-[2-hydroxyethyl]piperazine-N'-[2-hydroxypropanesulphonic]acid), POPSO (piperazie-N, N'-bis[2-hydroxypropanesulphonic]acid), TEA (triethanolamine), EPPS (N-[2-hydroxyethyl]-piperazine-N'-[3-propanesulphonic]acid), TRICINE (N-tris[hydroxymethyl]methylglycine), GLY-GLY (diglycine), BICINE (N,N-bis[2-hydroxyethyl]glycine), HEPBS (N-[2-hydroxyethyl]piperazine-N'-[4-butanesulphonic]acid), TAPS (N-tris[hydroxymethyl]methyl-3-aminopropanesulphonic acid), AMPD (2-amino-2-methyl-1,3-propanediol), TABS (N-tris[hydroxymethyl]methyl-4-aminobutanesulphonic acid), AMPSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid), and CABS (4-[cyclohexylamino]-1-butanesulphonic acid), preferably AMPD, TABS, AMPSO, CRES, CAPSO, AMP, CAPS or CABS.

The pH of the biological liquid in the buffer system, including the additive, can be between 2 and 12 However, for alkaline pH capillary electrophoresis, the pH is in the range 8 to 12, preferably in the range 9 to 11, more particularly preferably at about 10.

The buffer systems of the invention can also comprise at least one pH-modifying compound. The pH-modifying compound can be a compound selected from lithium hydroxide, sodium hydroxide, potassium hydroxide, rubidium hydroxide, caesium hydroxide, francium hydroxide, or a mono-, di-, tri- or tetra-alkyl ammonium hydroxide containing 1 to 8 carbon atoms in the alkyl portion.

In accordance with the invention, the biological buffers are used under the usual conditions, at concentrations in the buffer system of the order of 10 to 500 mM, preferably 20 to 200 mM.

The additives of the invention are used in concentrations of 0.1 mM to 500 mM without, however, exceeding their critical micellar concentration in the buffer system.

This value of the critical micellar concentration is applicable to additives that are surfactants.

When octanesulphonate is used, its concentration in the buffer is of the order of 1 to 5 mM, preferably 1 to 5 mM; preferably, the concentration is about 2.5 mM.

In the methods of the invention, the buffer system can also comprise sodium sulphate.

The buffer compositions of the invention are prepared in a manner that is normal when preparing buffer system compositions, namely by adding the constituents in the liquid form or as a solid to be diluted, to an acceptable support. Usually, the support is water, either distilled or demineralise.

The materials used for the capillaries are those routinely employed in capillary electrophoresis. It is possible to use fused silica capillaries with an internal diameter of 5 to 2000 μm. Preferably, capillaries with an internal diameter of less than 200 μm are used, more preferably less than 100 μm. Preferably, capillaries with an untreated internal surface are used The skilled person will be capable of adapting the nature and size of the capillary to the analytical requirements.

EXAMPLES

Materials and Methods

A) Capillary Electrophoresis (Method A)

Capillary electrophoresis was carried out on clinical samples using a CE apparatus provided with a fused silica capillary with an internal diameter of 25 microns. Detection was carried out at 200 nm. The samples were placed in the apparatus's sample changer and automatically injected by hydrodynamic injection (50 mbars for 7 s). The samples were separated within 10 minutes by applying an electrical field of about 400 V/cm. The capillary was washed with 0.5 M sodium hydroxide before each analysis, then with the buffer system.

Buffer Systems

Analytical grade chemical substances were used.

A 150 mM glycine buffer was prepared by dissolving 11.26 g of glycine (molar mass 75.07 g/mole) in 1 liter (l) of demineralised water. The final concentration was 150 mM and the pH was adjusted to 10.0 by adding sodium hydroxide pellets (molar mass: 40.0 g/mole).

A 150 mM borate buffer was prepared by dissolving 9.3 g of boric acid (molar mass 61.83 g/mole) in 1 l of demineralised water and 5.1 g of sodium hydroxide (molar mass: 40.0 g/mole). The final concentration was 150 mM and the pH was 10.0.

B) Agarose Gel Electrophoresis (Method B)

Agarose gel was used to carry out a comparative analysis of blood proteins. 10 μl of serum was loaded into each well in the membrane applicator described in European patent EP-A-0 493 996, U.S. Pat. Nos. 5,464,515 and 5,405,516. The loaded applicator was then applied to the surface of an agarose gel for 30 seconds. The samples applied to this agarose gel were separated by electrophoresis for about 7.5 minutes at a power of 20 W, using an instrument that could regulate the temperature to 20° C. After migration, the gel was dried and stained with acid black. After staining, the gel was decolorised and dried again The gels were then analysed by densitometry to produce the protein profiles.

C) Clinical Samples

For the CE, human serum was diluted to $1/10^{th}$ in the buffer system.

Example 1 (Comparative)

A glycine buffer system was prepared as described above. Normal serum was analysed.

Electrophoresis was carried out using method A above.

As can be seen from FIG. 1, the electropherograms obtained exhibits five successive peaks, attributed to the γ, β, $\alpha_2$, $\alpha_1$ globulin and albumin fractions respectively, reading from left to right.

Example 2

Octanesulphonate in a concentration of 2.5 mM was added to the buffer system of Example 1.

The electrophoresis was cried out as described in Example 1.

As can be seen in FIG. 2, the electropherogram obtained exhibits five successive peaks, attributed to γ, β, $\alpha_2$, $\alpha_1$ globulin and albumin fractions respectively. Comparison with the result of Example 1 shows that the separation between the two fractions, $\alpha_1$ globulin and albumin, is substantially improved, and the return to the base line is improved.

Example 3 (Comparative)

The procedure of Example 1 was followed, the buffer system being the borate buffer prepared as described above.

The electrophoresis was carried out as described in Example 1.

As can be seen in FIG. 3, the electropherogram obtained exhibits six successive peaks, attributed to γ, $\beta_2$, $\beta_1$, $\alpha_2$, $\alpha_1$ globulin and albumin fractions respectively.

Example 4

Octanesulphonate in a concentration of 2.5 mM was added to the buffer system of Example 3.

The electrophoresis was carried out as described in Example 1.

As can be seen in FIG. 4, the electropherogram obtained exhibits six successive peaks, attributed to γ, $\beta_2$, $\beta_1$, $\alpha_2$, $\alpha_1$ globulin and albumin fractions respectively. Separation between the two fractions, $\alpha_1$ globulin and albumin, is substantially improved, and the return to the base line is improved.

Example 5 (Comparative)

The electropherogram of FIG. 5 was obtained by analysing the same serum as in the preceding examples using method B above. Comparison with the result obtained in Examples 2 and 4 shows that these implementations can produce a resolution that is substantially comparable to the resolution obtained with an agarose gel.

Example 6 (Comparative)

A 150 mM glycine buffer system was prepared.

Serum with high $\alpha_1$ and $\alpha_2$ globulin contents was analysed.

The electrophoresis was carried out as described in Example 1.

As can be seen in FIG. 6, the electropherogram obtained exhibits five successive peaks, attributed to γ, β, $\alpha_2$, $\alpha_1$ globulin and albumin fractions respectively.

Example 7

Octanesulphonate in a concentration of 2.5 mM was added to the buffer system of Example 6.

The electrophoresis was carried out as described in Example 6.

As can be seen in FIG. 7, the electropherogram obtained exhibits five successive peaks, attributed to γ, β, $α_2$, $α_1$ globulin and albumin fractions respectively. Comparison with the result of Example 6 shows that the separation between the two fractions, $α_1$ globulin and album is substantially improved, and the return to the base line is improved.

Example 8 (Comparative)

The procedure of Example 6 was followed, the buffer being a 150 mM borate buffer.

The electrophoresis was carried out as described in Example 6.

As can be seen in FIG. 8, the electropherogram obtained exhibits six successive peaks, attributed to γ, $β_2$, $β_1$, $α_2$, $α_1$ globulin ad albumin fractions respectively.

Example 9

Octanesulphonate in a concentration of 2.5 mM was added to the buffer system of Example 8.

The electrophoresis was carried out as described in Example 6.

As can be seen in FIG. 9, the electropherogram obtained under the same conditions exhibits six successive peaks, attributed to γ, $β_2$, $β_1$, $α_2$, $α_1$ globulin and albumin fractions respectively. Separation between the two fractions, $α_1$ globulin and albumin, is substantially improved, and the return to the base line is improved. The $α_1$ fraction can be seen to be composed of two peaks, one of which corresponds to the orosomucoid and, in the absence of octanesulphonate, being merged with the albumin peak.

Example 10 (Comparative)

The electropherogram of FIG. 10 was obtained by analysing the same serum as in Examples 6 to 9 using method B above. Comparison with the result obtained in Examples 7 and 9 showed that these implementations can produce a resolution that is substantially comparable to the resolution obtained with an agarose gel.

Example 11

The comparative mobility ($mn^{-1}$) of $α_1$ globulin and albumin were measured in a borate buffer (150 mM) with a pH of 10, using method A above. Alkylsulphonates with an increasing alkyl chain length (n) (n represents 4, 6, 8 and 10 respectively for $C_4$, $C_6$, $C_8$ and $C_{10}$, and n=0 corresponds to a buffer with no alkylsulphonate) were added to the borate buffer in a concentration of 2.5 mM. The mobilities of the alpha-1 fractions and the albu fractions were calculated and are shown on the graph of FIG. 11. A substantial drop in the mobility of the albumin (■) compared with that of the alpha-1 fraction (♦) can be seen beyond a C6 chain.

The invention claimed is:

1. An alkaline pH, free solution capillary electrophoresis process for analyzing a human biological sample comprising serum protein constituents including albumin and at least one other constituent selected from $α_1$-globulin, $α_2$-globulin, β-globulin, $β_1$-globulin, $β_2$-globulin and γ-globulin, said method comprising: introducing the human biological sample into a capillary tube containing a buffer system, wherein said buffer system comprises a buffer and at least one additive having a hydrophobic interaction with said albumin constituent and providing said albumin constituent with at least one negative charge thereby reducing the electrophoretic mobility of said albumin.

2. The method of claim 1, which further comprises separating said protein constituents by migrating and detecting said constituents.

3. The method of claim 1, wherein the sample is serum, hemolyzed blood, plasma, urine or cerebrospinal fluid.

4. The method of claim 1, wherein said constituents are serum proteins.

5. The method of claim 1, wherein said at least one additive comprises an anionic pole with a pH of more than 9 and a hydrophobic portion.

6. The method of claim 1, wherein said additive comprises a hydrophobic portion composed of at least one linear or non linear alkyl chain containing 4 to 22 carbon atoms, and/or at least a combination of 1 to 10 aromatic or non-aromatic cycles, and an anionic pole constituted by one or more groups selected from sulphonates, carboxylates, sulphates, phosphates and carbonates.

7. The method of claim 1, wherein said additive is selected from cholates, $C_6$ to $C_{22}$ alkyl-mono-, di- or tri-sulphonates, tetradecenesulphonate, naphthalenesulphonates, $C_6$ to $C_{22}$ alkymono-, di- or tri-carboxylates, $C_6$ to $C_{22}$ alkylcarboxysulphonates, naphthalenecarboxylates, $C_4$ to $C_{14}$ alkylsulphates, $C_4$ to $C_{14}$ alkylcarbonates, benzenesulphonates and benzenecarboxylates.

8. The method of claim 1, wherein said additive is a $C_6$ to $C_{10}$ alkylsulphonate.

9. The method of claim 1, wherein said additive is octanesulphonate.

10. The method of claim 1, wherein said additive has a concentration in said buffer system in the range of 0.1 mM to 500 mM.

11. The method of claim 10, wherein said additive in said buffer system does not exceed the critical micellar concentration of said additive in said buffer.

12. The method of claim 1, wherein said additive has a concentration in the range of 1 mM to 4 mM in said buffer system.

13. The method of claim 1, wherein said additive has a concentration of about 2.5 mM in the buffer system.

14. The method of claim 1, wherein said buffer system has a pH in the range of 9 to 11.

15. The method of claim 1, wherein the capillary tube is fused silica.

16. The method of claim 1, wherein said buffer system further comprises at least one pH-modifying agent.

17. The method of claim 16, wherein the pH-modifying agent is selected from lithium hydroxide, sodium hydroxide, potassium hydroxide, rubidium hydroxide, cesium hydroxide, francium hydroxide, or a mono-, di-, tri- or tetra-alkyl ammonium hydroxide containing 1 to 8 carbon atoms in the alkyl portion.

18. The method according to claim 1, wherein said additive is a zwitterionic biological buffer.

19. The method of claim 1, wherein said additive is a linear $C_6$-$C_{10}$-alkylsulphonate.

20. The method of claim 1, wherein said additive is n-octylsulphonate.

21. A method for separating protein constituents in a human biological sample comprising albumin and at least one serum protein selected from $α_1$-globulin, $α_2$-globulin, β-globulin, $β_1$-globulin, $β_2$-globulin and γ-globulin, said method comprising passing said serum protein constituents into a capillary containing a buffer system comprising at least one buffer and at least one additive having a hydrophobic interaction with human albumin, wherein the electrophoretic mobility of said albumin is reduced.

22. A method for separating protein constituents in a human biological sample comprising albumin and at least one serum protein selected from $\alpha_1$-globulin, $\alpha_2$-globulin, $\beta$-globulin, $\beta_1$-globulin, $\beta_2$-globulin and $\gamma$-globulin said method comprising passing said serum protein constituents into a capillary containing a buffer system comprising at least one buffer and at least one additive, wherein said additive is a compound comprising an anionic pole with a pH of more than 9 and a hydrophobic portion, wherein said additive reduces the electrophoretic mobility of said albumin.

23. The method according to claim 1 or 21 or 22, wherein said buffer system further comprises sodium sulphate.

24. An alkaline pH, free solution capillary electrophoresis process for analyzing a human biological sample comprising serum protein constituents including albumin and at least one other constituent selected from $\alpha_1$-globulin, $\alpha_2$-globulin, $\beta$-globulin, $\beta_1$-globulin, $\beta_2$-globulin and $\gamma$-globulin, said method comprising:

introducing the human biological sample into a capillary tube containing a buffer system wherein said buffer system has a pH in the range of 9 to 11 and wherein said buffer system comprises a buffer and at least one additive selected from cholates, $C_6$ to $C_{22}$ alkyl-mono-, di- or tri-sulphonates, tetradecenesulphonate, naphthalenesulphonates, $C_6$ to $C_{22}$ alkymono-, di- or tri-carboxylates, $C_6$ to $C_{22}$ alkylcarboxysulphonates, naphthalenecarboxylates, $C_4$ to $C_{14}$ alkylsulphates, $C_4$ to $C_{14}$ alkylcarbonates, benzenesulphonates and benzenecarboxylates and having a hydrophobic interaction with said albumin constituent and providing said albumin constituent with at least one negative charge thereby reducing the electrophoretic mobility of said albumin.

* * * * *

UNITED STATES PATENT AND TRADEMARK OFFICE
CERTIFICATE OF CORRECTION

PATENT NO. : 7,297,244 B2
APPLICATION NO. : 10/052931
DATED : November 20, 2007
INVENTOR(S) : Georges Nouadje and Frédéric Robert It is certified that error appears in the above-identified patent and that said Letters Patent is hereby corrected as shown below:

Column 1, line 61 before "albumin" insert --the--.
Column 2, line 2 after "portion" insert --.--.
Column 3, line 18, "The" should start a new paragraph.
Column 4, line 42 after "12" insert --.--.
Column 6, line 10 "cried" should read --carried--.

Signed and Sealed this

Twenty-eighth Day of October, 2008

JON W. DUDAS
*Director of the United States Patent and Trademark Office*